(12) United States Patent
Foster

(10) Patent No.: US 8,688,236 B2
(45) Date of Patent: *Apr. 1, 2014

(54) MEDICAL LEAD COIL CONDUCTOR WITH SPACER ELEMENT

(75) Inventor: Arthur J. Foster, Centerville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 5 days.

This patent is subject to a terminal disclaimer.

(21) Appl. No.: 13/324,007

(22) Filed: Dec. 13, 2011

(65) Prior Publication Data

US 2012/0109270 A1    May 3, 2012

Related U.S. Application Data

(63) Continuation of application No. 12/411,681, filed on Mar. 26, 2009, now Pat. No. 8,103,360.

(60) Provisional application No. 61/051,927, filed on May 9, 2008.

(51) Int. Cl.
    *A61N 1/05*    (2006.01)

(52) U.S. Cl.
    USPC .......................................................... 607/122

(58) Field of Classification Search
    USPC .......................................................... 607/122
    See application file for complete search history.

(56) References Cited

U.S. PATENT DOCUMENTS

| | | | |
|---|---|---|---|
| 3,614,692 A | 10/1971 | Rozelle et al. | |
| 4,131,759 A | 12/1978 | Felkel | |
| 4,135,518 A | 1/1979 | Dutcher | |
| 4,404,125 A | 9/1983 | Abolins et al. | |
| 4,484,586 A | 11/1984 | McMickle et al. | |
| 4,493,329 A | 1/1985 | Crawford et al. | |
| 4,643,203 A | 2/1987 | Labbe | |
| 4,869,970 A | 9/1989 | Gulla et al. | |
| 5,056,516 A | 10/1991 | Spehr | |
| 5,217,010 A | 6/1993 | Tsitlik et al. | |
| 5,222,506 A | 6/1993 | Patrick et al. | |
| 5,231,996 A | 8/1993 | Bardy et al. | |
| 5,241,957 A | 9/1993 | Camp et al. | |
| 5,243,911 A | 9/1993 | Dow et al. | |

(Continued)

FOREIGN PATENT DOCUMENTS

| | | |
|---|---|---|
| CN | 1762510 A | 4/2006 |
| CN | 101039619 A | 9/2007 |

(Continued)

OTHER PUBLICATIONS

Gray, Robert W. et al., "Simple design changes to wires to substantially reduce MRI-induced heating at 1.5 T: implications for implanted leads", Magnetic Resonance Imaging 23 (2005) 887-891.

(Continued)

*Primary Examiner* — Kennedy Schaetzle

(74) *Attorney, Agent, or Firm* — Faegre Baker Daniels LLP

(57) ABSTRACT

Medical electrical leads equipped with spacer elements and configured for use during medical procedures such as magnetic resonance imaging (MRI) are disclosed. An illustrative medical electrical lead includes a proximal connector, an insulated lead body including at least one electrode, a helically coiled conductor wire, and a helically coiled spacer element interstitially disposed between adjacent turns of the conductor wire.

20 Claims, 7 Drawing Sheets

(56) References Cited

U.S. PATENT DOCUMENTS

| | | |
|---|---|---|
| 5,246,014 A | 9/1993 | Williams et al. |
| 5,330,522 A | 7/1994 | Kreyenhagen |
| 5,354,327 A | 10/1994 | Smits |
| 5,378,234 A | 1/1995 | Hammerslag et al. |
| 5,387,199 A | 2/1995 | Siman et al. |
| 5,425,755 A | 6/1995 | Doan |
| 5,456,707 A | 10/1995 | Giele |
| 5,483,022 A | 1/1996 | Mar |
| 5,522,872 A | 6/1996 | Hoff |
| 5,522,875 A | 6/1996 | Gates et al. |
| 5,554,139 A | 9/1996 | Okajima |
| 5,574,249 A | 11/1996 | Lindsay |
| 5,584,873 A | 12/1996 | Shoberg et al. |
| 5,599,576 A | 2/1997 | Opolski |
| 5,609,622 A | 3/1997 | Soukup et al. |
| 5,618,208 A | 4/1997 | Crouse et al. |
| 5,728,149 A | 3/1998 | Laske et al. |
| 5,760,341 A | 6/1998 | Laske et al. |
| 5,800,496 A | 9/1998 | Swoyer et al. |
| 5,810,887 A | 9/1998 | Accorti, Jr. et al. |
| 5,833,715 A | 11/1998 | Vachon et al. |
| 5,935,159 A | 8/1999 | Cross, Jr. et al. |
| 5,957,966 A | 9/1999 | Schroeppel et al. |
| 5,957,970 A | 9/1999 | Shoberg et al. |
| 5,968,087 A | 10/1999 | Hess et al. |
| 6,057,031 A | 5/2000 | Breme et al. |
| 6,078,840 A | 6/2000 | Stokes |
| 6,083,216 A | 7/2000 | Fischer, Sr. |
| 6,106,522 A | 8/2000 | Fleischman et al. |
| 6,141,593 A | 10/2000 | Patag |
| 6,143,013 A | 11/2000 | Samson et al. |
| 6,178,355 B1 | 1/2001 | Williams et al. |
| 6,208,881 B1 | 3/2001 | Champeau |
| 6,249,708 B1 | 6/2001 | Nelson et al. |
| 6,256,541 B1 | 7/2001 | Heil et al. |
| 6,259,954 B1 | 7/2001 | Conger et al. |
| 6,289,250 B1 | 9/2001 | Tsuboi et al. |
| 6,295,476 B1 | 9/2001 | Schaenzer |
| 6,400,992 B1 | 6/2002 | Borgersen et al. |
| 6,434,430 B2 | 8/2002 | Borgersen et al. |
| 6,456,888 B1 | 9/2002 | Skinner et al. |
| 6,493,591 B1 | 12/2002 | Stokes |
| 6,501,991 B1 | 12/2002 | Honeck et al. |
| 6,501,994 B1 | 12/2002 | Janke et al. |
| 6,510,345 B1 | 1/2003 | Van Bentem |
| 6,516,230 B2 | 2/2003 | Williams et al. |
| 6,526,321 B1 | 2/2003 | Spehr |
| 6,564,107 B1 | 5/2003 | Bodner et al. |
| 6,671,554 B2 | 12/2003 | Gibson et al. |
| 6,721,604 B1 | 4/2004 | Robinson et al. |
| 6,813,251 B1 | 11/2004 | Garney et al. |
| 6,850,803 B1 | 2/2005 | Jimenez et al. |
| 6,854,994 B2 | 2/2005 | Stein et al. |
| 6,920,361 B2 | 7/2005 | Williams |
| 6,925,334 B1 | 8/2005 | Salys |
| 6,949,929 B2 | 9/2005 | Gray et al. |
| 6,978,185 B2 | 12/2005 | Osypka |
| 6,993,373 B2 | 1/2006 | Vrijheid et al. |
| 6,999,821 B2 | 2/2006 | Jenney et al. |
| 7,013,180 B2 | 3/2006 | Dublin et al. |
| 7,013,182 B1 | 3/2006 | Krishnan |
| 7,123,013 B2 | 10/2006 | Gray |
| 7,138,582 B2 | 11/2006 | Lessar et al. |
| 7,158,837 B2 | 1/2007 | Osypka et al. |
| 7,174,219 B2 | 2/2007 | Wahlstrand et al. |
| 7,174,220 B1 | 2/2007 | Chitre et al. |
| 7,205,768 B2 | 4/2007 | Schulz et al. |
| 7,257,449 B2 | 8/2007 | Bodner |
| 7,363,090 B2 | 4/2008 | Halperin et al. |
| 7,378,931 B2 | 5/2008 | Odahara et al. |
| 7,388,378 B2 | 6/2008 | Gray et al. |
| 7,389,148 B1 | 6/2008 | Morgan |
| 7,453,344 B2 | 11/2008 | Maeda et al. |
| 7,571,010 B2 | 8/2009 | Zarembo et al. |
| 7,610,101 B2 | 10/2009 | Wedan et al. |
| 7,765,005 B2 | 7/2010 | Stevenson |
| 7,917,213 B2 | 3/2011 | Bulkes et al. |
| 7,986,999 B2 | 7/2011 | Wedan et al. |
| 8,103,360 B2 | 1/2012 | Foster |
| 8,170,688 B2 | 5/2012 | Wedan et al. |
| 8,244,346 B2 | 8/2012 | Foster et al. |
| 8,391,994 B2 | 3/2013 | Foster et al. |
| 8,401,671 B2 | 3/2013 | Wedan et al. |
| 2002/0065544 A1* | 5/2002 | Smits ........................ 607/122 |
| 2002/0072769 A1 | 6/2002 | Silvian et al. |
| 2002/0111664 A1 | 8/2002 | Bartig et al. |
| 2002/0128689 A1 | 9/2002 | Connelly et al. |
| 2002/0144720 A1 | 10/2002 | Zahorik et al. |
| 2003/0050680 A1 | 3/2003 | Gibson et al. |
| 2003/0063946 A1 | 4/2003 | Williams et al. |
| 2003/0083723 A1 | 5/2003 | Wilkinson et al. |
| 2003/0083726 A1 | 5/2003 | Zeijlemaker et al. |
| 2003/0092303 A1 | 5/2003 | Osypka |
| 2003/0093138 A1 | 5/2003 | Osypka et al. |
| 2003/0139794 A1 | 7/2003 | Jenney et al. |
| 2003/0140931 A1 | 7/2003 | Zeijlemaker et al. |
| 2003/0144705 A1 | 7/2003 | Funke |
| 2003/0144716 A1 | 7/2003 | Reinke et al. |
| 2003/0144718 A1 | 7/2003 | Zeijlemaker |
| 2003/0144719 A1 | 7/2003 | Zeijlemaker |
| 2003/0144720 A1 | 7/2003 | Villaseca et al. |
| 2003/0144721 A1 | 7/2003 | Villaseca et al. |
| 2003/0204217 A1 | 10/2003 | Greatbatch |
| 2004/0014355 A1 | 1/2004 | Osypka et al. |
| 2004/0064173 A1 | 4/2004 | Hine et al. |
| 2004/0064174 A1 | 4/2004 | Belden |
| 2004/0088033 A1 | 5/2004 | Smits et al. |
| 2004/0122490 A1 | 6/2004 | Reinke et al. |
| 2004/0162600 A1 | 8/2004 | Williams |
| 2004/0193140 A1 | 9/2004 | Griffin et al. |
| 2004/0243210 A1 | 12/2004 | Morgan et al. |
| 2004/0267107 A1 | 12/2004 | Lessar et al. |
| 2005/0030322 A1 | 2/2005 | Gardos |
| 2005/0070972 A1 | 3/2005 | Wahlstrand et al. |
| 2005/0090886 A1 | 4/2005 | MacDonald et al. |
| 2005/0113676 A1 | 5/2005 | Weiner et al. |
| 2005/0113873 A1 | 5/2005 | Weiner et al. |
| 2005/0113876 A1 | 5/2005 | Weiner et al. |
| 2005/0182471 A1 | 8/2005 | Wang |
| 2005/0222642 A1 | 10/2005 | Przybyszewski et al. |
| 2005/0222656 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2005/0246007 A1 | 11/2005 | Sommer et al. |
| 2005/0272280 A1 | 12/2005 | Osypka |
| 2005/0283167 A1 | 12/2005 | Gray |
| 2006/0009819 A1 | 1/2006 | Przybyszewski |
| 2006/0030774 A1 | 2/2006 | Gray et al. |
| 2006/0041294 A1 | 2/2006 | Gray |
| 2006/0089691 A1 | 4/2006 | Kaplan et al. |
| 2006/0089695 A1 | 4/2006 | Bolea et al. |
| 2006/0089696 A1 | 4/2006 | Olsen et al. |
| 2006/0093685 A1 | 5/2006 | Mower et al. |
| 2006/0105066 A1 | 5/2006 | Teague et al. |
| 2006/0106442 A1 | 5/2006 | Richardson et al. |
| 2006/0167536 A1 | 7/2006 | Nygren et al. |
| 2006/0200218 A1 | 9/2006 | Wahlstrand |
| 2006/0229693 A1 | 10/2006 | Bauer et al. |
| 2006/0247747 A1 | 11/2006 | Olsen et al. |
| 2006/0247748 A1 | 11/2006 | Wahlstrand et al. |
| 2006/0271138 A1 | 11/2006 | MacDonald |
| 2006/0293737 A1 | 12/2006 | Krishnan |
| 2007/0106332 A1 | 5/2007 | Denker et al. |
| 2007/0112398 A1 | 5/2007 | Stevenson et al. |
| 2007/0156205 A1 | 7/2007 | Larson et al. |
| 2007/0179577 A1 | 8/2007 | Marshall et al. |
| 2007/0179582 A1 | 8/2007 | Marshall et al. |
| 2007/0191914 A1 | 8/2007 | Stessman |
| 2007/0208383 A1 | 9/2007 | Williams |
| 2008/0033497 A1 | 2/2008 | Bulkes et al. |
| 2008/0039709 A1 | 2/2008 | Karmarkar |
| 2008/0049376 A1 | 2/2008 | Stevenson et al. |
| 2008/0058902 A1 | 3/2008 | Gray et al. |

(56) References Cited

U.S. PATENT DOCUMENTS

| | | |
|---|---|---|
| 2008/0125754 A1 | 5/2008 | Beer et al. |
| 2008/0129435 A1 | 6/2008 | Gray |
| 2008/0132986 A1 | 6/2008 | Gray et al. |
| 2008/0243218 A1 | 10/2008 | Bottomley et al. |
| 2008/0262584 A1 | 10/2008 | Bottomley et al. |
| 2009/0099440 A1 | 4/2009 | Viohl |
| 2009/0099555 A1 | 4/2009 | Viohl et al. |
| 2009/0118610 A1 | 5/2009 | Karmarkar et al. |
| 2009/0149920 A1 | 6/2009 | Li et al. |
| 2009/0149933 A1 | 6/2009 | Ameri |
| 2009/0198314 A1 | 8/2009 | Foster et al. |
| 2009/0270956 A1 | 10/2009 | Vase et al. |
| 2009/0281608 A1 | 11/2009 | Foster |
| 2010/0010602 A1 | 1/2010 | Wedan et al. |
| 2010/0114277 A1 | 5/2010 | Zhao et al. |
| 2010/0174348 A1 | 7/2010 | Bulkes et al. |
| 2010/0234929 A1 | 9/2010 | Scheuermann |
| 2010/0331936 A1 | 12/2010 | Perrey et al. |
| 2011/0079423 A1 | 4/2011 | Zhao et al. |
| 2011/0087299 A1 | 4/2011 | Ameri |
| 2011/0093054 A1 | 4/2011 | Ameri et al. |
| 2011/0160817 A1 | 6/2011 | Foster et al. |
| 2011/0160818 A1 | 6/2011 | Struve |
| 2011/0160828 A1 | 6/2011 | Foster et al. |
| 2011/0160829 A1 | 6/2011 | Foster et al. |
| 2011/0208280 A1 | 8/2011 | Li et al. |
| 2011/0218422 A1 | 9/2011 | Atalar et al. |
| 2011/0238146 A1 | 9/2011 | Wedan et al. |
| 2011/0288403 A1 | 11/2011 | Kondabatni et al. |
| 2012/0016451 A1 | 1/2012 | Struve et al. |
| 2012/0022356 A1 | 1/2012 | Olsen et al. |
| 2012/0035698 A1 | 2/2012 | Johnson et al. |
| 2012/0053662 A1 | 3/2012 | Foster et al. |
| 2012/0161901 A1 | 6/2012 | Stevenson et al. |
| 2012/0179233 A1 | 7/2012 | Wedan et al. |
| 2012/0253340 A1 | 10/2012 | Stevenson et al. |
| 2012/0271394 A1 | 10/2012 | Foster et al. |
| 2013/0116764 A1 | 5/2013 | Walker et al. |
| 2013/0158641 A1 | 6/2013 | Foster et al. |
| 2013/0190850 A1 | 7/2013 | Wedan et al. |

FOREIGN PATENT DOCUMENTS

| | | |
|---|---|---|
| EP | 0897997 B1 | 2/2003 |
| EP | 1594564 A1 | 11/2005 |
| JP | 2004141679 A | 5/2004 |
| JP | 2005501673 A | 1/2005 |
| JP | 2005515852 A | 6/2005 |
| JP | 2005515854 A | 6/2005 |
| WO | WO9606655 A1 | 3/1996 |
| WO | WO03089045 A2 | 10/2003 |
| WO | WO2004073791 A1 | 9/2004 |
| WO | WO2006105066 A2 | 3/2006 |
| WO | WO2006093685 A1 | 9/2006 |
| WO | WO2007047966 A2 | 4/2007 |
| WO | WO2007089986 A1 | 8/2007 |
| WO | WO2007118194 A2 | 10/2007 |
| WO | WO2010078552 A1 | 7/2010 |

OTHER PUBLICATIONS

International Search Report and Written Opinion issued in PCT/US2008/085518 on Oct. 29, 2009, 15 pages.

International Search Report and Written Opinion issued in PCT/US2009/038629, mailed Jun. 29, 2009, 11 pages.

International Search Report and Written Opinion issued in PCT/US2010/024062, mailed Sep. 27, 2010.

International Search Report and Written Opinion issued in PCT/US2010/033686 on Aug. 10, 2010, 12 pages.

Invitation to Pay Additional Fees and Partial Search Report, dated Aug. 17, 2009, issued in PCT/US2008/085533, 6 pages.

Invitation to Pay Additional Fees and Partial Search Report, issued in PCT/US2010/024062, mailed May 7, 2010.

International Search Report and Written Opinion issued in PCT/US2010/055653, mailed Feb. 1, 2011, 14 pages.

International Search Report and Written Opinion issued in PCT/US2010/055130, mailed Mar. 10, 2011, 11 pages.

International Search Report and Written Opinion issued in PCT/US2009/032838, mailed May 4, 2009, 14 pages.

International Search Report and Written Opinion issued in PCT/US2012/055673, mailed Dec. 13, 2012, 10 pages.

* cited by examiner

MEDICAL LEAD COIL CONDUCTOR WITH SPACER ELEMENT

CROSS-REFERENCE TO RELATED APPLICATIONS

This application is a continuation of U.S. application Ser. No. 12/411,681, filed on Mar. 26, 2009, which claims priority under 35 U.S.C. §119 to U.S. Provisional Application No. 61/051,927, filed on May 9, 2008, both entitled "MEDICAL LEAD COIL CONDUCTOR WITH SPACER ELEMENT," each of which are incorporated herein by reference in their entirety for all purposes.

TECHNICAL FIELD

The present invention relates to implantable medical devices for stimulating body tissues and/or sensing physiological attributes. More specifically, the present invention relates to medical electrical leads that dissipate and/or deflect electromagnetic energy during medical procedures such as magnetic resonance imaging (MRI).

BACKGROUND

Magnetic resonance imaging (MRI) is a non-invasive imaging method that utilizes nuclear magnetic resonance techniques to render images within a patient's body. Typically, MRI systems employ the use of a magnetic coil having a magnetic field strength of between about 0.2 to 3 Teslas. During the procedure, the body tissue is briefly exposed to RF pulses of electromagnetic energy in a plane perpendicular to the magnetic field. The resultant electromagnetic energy from these pulses can be used to image the body tissue by measuring the relaxation properties of the excited atomic nuclei in the tissue.

During imaging, the electromagnetic radiation produced by the MRI system may be picked up by implantable device leads used in implantable medical devices such as pacemakers or cardiac defibrillators. This energy may be transferred through the lead to the electrode in contact with the tissue, which may lead to elevated temperatures at the point of contact. The degree of tissue heating is typically related to factors such as the length of the lead, the conductivity or impedance of the lead, and the surface area of the lead electrodes. Exposure to a magnetic field may also induce an undesired voltage in the lead.

SUMMARY

The present invention relates to medical electrical leads configured to dissipate and/or deflect electromagnetic energy during medical procedures such as magnetic resonance imaging (MRI). An illustrative medical electrical lead includes a proximal connector configured to couple the lead to an implantable medical device, and an insulated lead body coupled to the proximal connector and including at least one electrode for use in providing therapeutic stimulus energy to the body and/or for sensing electrical activity within the body. The lead includes at least one helically coiled conductor wire electrically coupled to an electrode, and at least one non-conductive spacer element electrically isolated from the electrode. The turns of the spacer element are interstitially disposed between the turns of the conductor coil, and in some embodiments include a conductive inner core that can be used to dissipate electromagnetic energy along the length of the lead.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
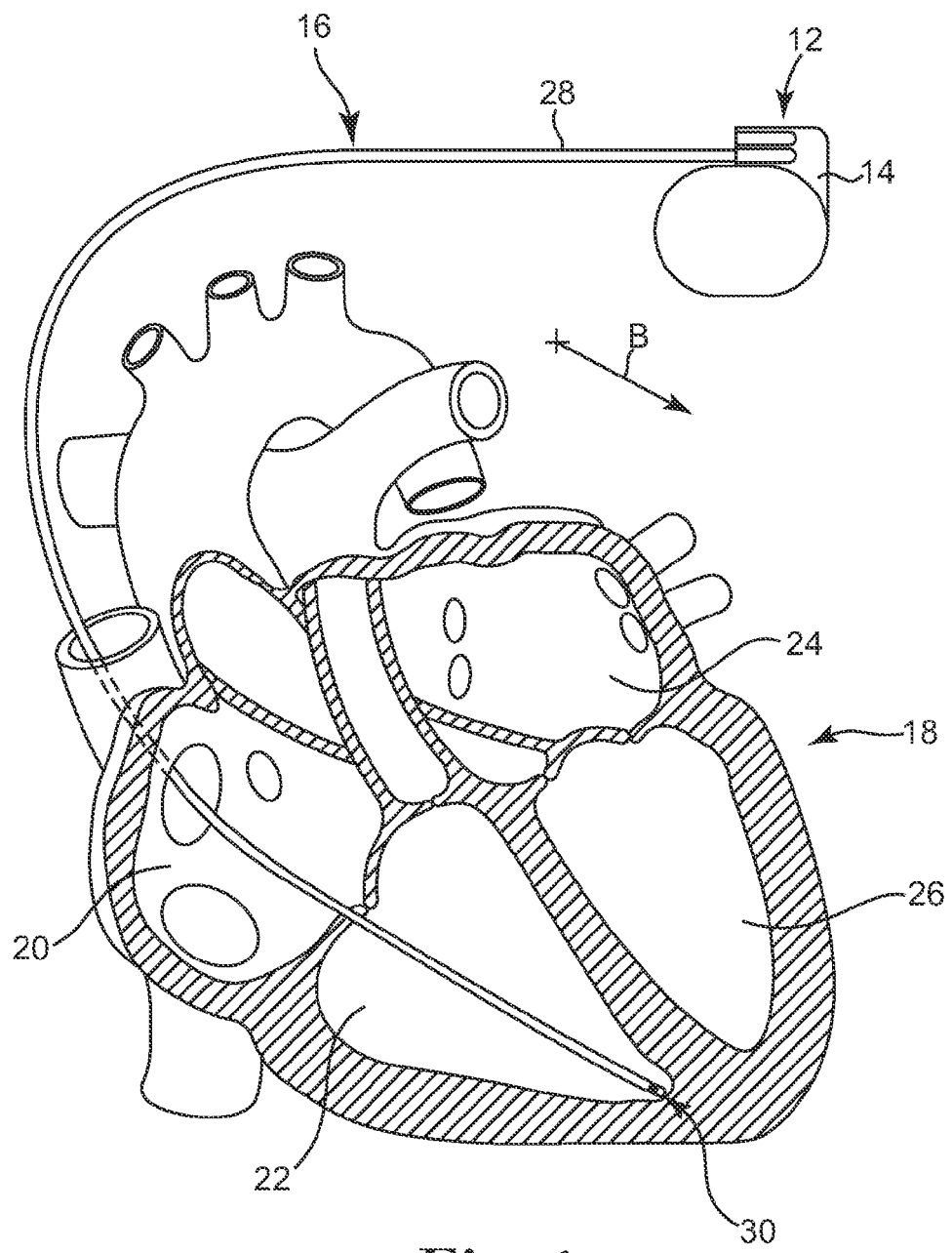
FIG. 1 is a schematic view showing an implantable medical device including a lead implanted within the heart of a patient.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view showing an implantable medical device 12 including a lead implanted within the body of a patient. In the illustrative embodiment depicted, the implantable medical device 12 includes a pulse generator 14 implanted within the patient's body and a lead 16 (e.g., a unipolar or bipolar lead) placed at a location in or near the patient's heart 18. The heart 18 includes a right atrium 20, a right ventricle 22, a left atrium 24, and a left ventricle 26. The pulse generator 14 can be implanted subcutaneously within the body, typically at a location such as in the patient's chest or abdomen, although other implantation locations are possible.

A proximal portion 28 of the lead 16 can be coupled to or formed integrally with the pulse generator 14. A distal tip portion 30 of the lead 16, in turn, can be implanted at a desired location in or near the heart 18 such as the right ventricle 22, as shown. Although the illustrative embodiment depicts only a single lead 16 inserted into the patient's heart 18, in other embodiments multiple leads can be utilized so as to electrically stimulate other areas of the heart 18. In some embodiments, for example, the distal portion of a second lead (not shown) may be implanted in the right atrium 20. In addition, or in lieu, another lead may be implanted in or near the left side of the heart 18 (e.g., in the coronary veins) to stimulate the left side of the heart 18. Other types of leads such as epicardial leads may also be utilized in addition to, or in lieu of, the lead 16 depicted in FIG. 1.

During operation, the lead 16 can be configured to convey electrical signals from the pulse generator 14 to the heart 18. For example, in those embodiments where the pulse generator 14 is a pacemaker, the lead 16 can be used to deliver electrical therapeutic stimulus for pacing the heart 18. In those embodiments where the pulse generator 14 is an implantable cardiac defibrillator, the lead 16 can be used to deliver electric shocks to the heart 18 in response to an event such as a heart attack or ventricular tachycardia. In some embodiments, the pulse generator 14 includes both pacing and defibrillation capabilities.

When the pulse generator 14 is subjected to a gradient magnetic field, as shown generally by arrow "B" in FIG. 1, a magnetically-induced voltage may be induced on the lead 16 that interferes with the therapeutic electrical signals normally delivered by the lead 16. During an MRI procedure, for example, a rapidly changing magnetic field B produced by an energized MRI coil may induce a voltage on the lead 16 that combines with the excitation voltage normally generated by the pulse generator 14 for providing therapy. This voltage is transmitted as a current on the lead 16 along with the desired therapeutic stimulus current produced by the pulse generator 14. During operation, this voltage can result in undesirable currents on the lead 16 that are then transmitted into the surrounding cardiac tissue.

Figure 2:
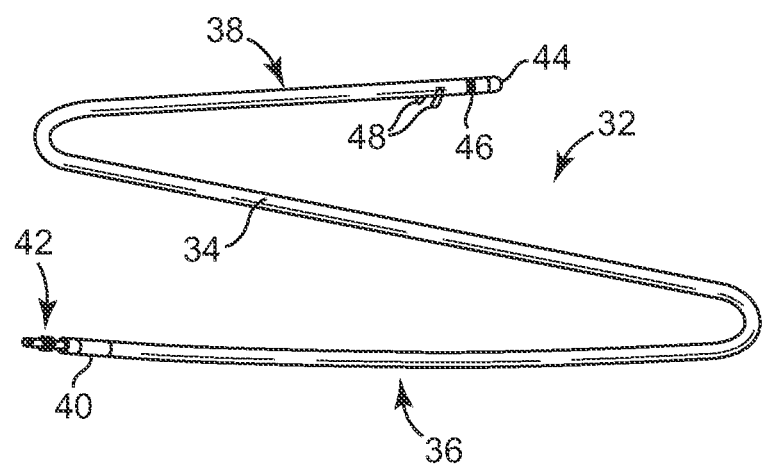
FIG. 2 is a perspective view of a medical electrical lead in accordance with an illustrative embodiment.

FIG. 2 is a perspective view of a medical electrical lead 32 in accordance with an illustrative embodiment. As shown in FIG. 2, the lead 32 includes an elongated lead body 34 having a proximal section 36 and a distal section 38. The proximal section 36 of the lead 32 has a proximal end 40, which in some embodiments is coupled to a hub connector 42 for use in connecting the lead 32 to an implantable medical device such as a pulse generator. The distal section 38 of the lead 32 terminates in a distal lead tip 44, which in some embodiments includes a distal electrode 46 for transmitting a therapeutic stimulus to the heart and/or for sensing electrical activity occurring in the heart. The lead 32 can further include one or more other electrodes in addition to, or in lieu of, the distal electrode 46. In a bipolar lead, for example, the lead 32 can include a pair of distal electrodes 46 for providing bipolar electrical energy to the heart.

The lead body 34 may be constructed of a flexible, electrically non-conductive material that permits the lead 32 to bend or flex to facilitate insertion of the lead 32 through the patient's body to a desired implantation site. In some embodiments, the lead 32 includes a means to attach the lead 32 to adjacent tissue within the body. For example, in some embodiments the lead 32 includes a number of barbs or tines 48 that facilitate attachment of the distal section 38 of the lead 32 to an inner wall of the heart or at some other desired location within the body.

As discussed further herein with respect to several embodiments, the lead 32 can be configured to dissipate and/or deflect electromagnetic or RF energy picked up by the lead 32, which can cause tissue heating at the interface of the electrode 46 and the surrounding tissue. In some embodiments, for example, the lead 32 can be configured to dissipate and/or deflect electromagnetic energy caused by a gradient magnetic field B produced by an energized MRI coil during magnetic resonance imaging. The lead 32 can be further configured to dissipate and/or deflect electromagnetic energy or RF energy produced by other sources of magnetic interference within the patient's body.

Figure 3:
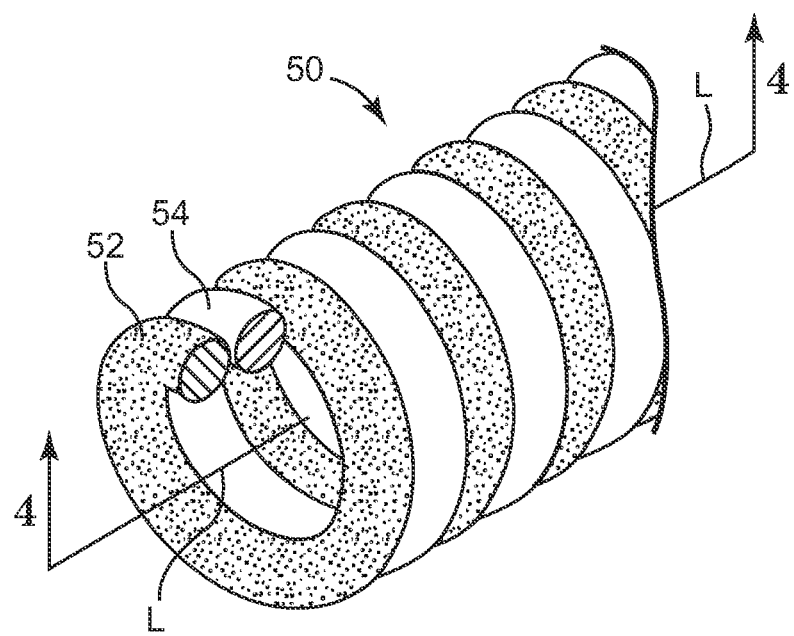
FIG. 3 is a partial cross-sectional view showing an illustrative conductor coil assembly for use with the medical electrical lead of FIG. 2.

FIG. 3 is a partial cross-sectional view showing an illustrative conductor coil assembly 50 for use with the medical electrical lead 32 of FIG. 2. As shown in FIG. 3, the conductor coil assembly 50 includes a single filar conductor coil 52 helically disposed about the longitudinal axis L of the assembly 50. The conductor coil 52 may be coupled proximally to electrical feedthroughs or connectors on the pulse generator 14, and may extend along all or a portion of the length of the lead body 34, terminating distally at one or more distal electrodes. With respect to the lead 32 of FIG. 2, for example, the conductor coil 52 may be electrically connected at its proximal end (not shown) to an implantable medical device (e.g., the pulse generator 14), and may extend along the length of the lead body 34 to one or more distal electrodes 46 on the lead 32.

In use, the conductor coil 52 can be configured to deliver electrical energy through the lead body 34 to the electrodes 46, which in some embodiments can be used for providing stimulus therapy to the patient and/or for sensing electrical impedance or other parameters within the patient's body. In some embodiments, for example, the conductor coil 52 may be used in conjunction with a unipolar lead to deliver electrical energy to heart tissue adjacent to the distal lead tip 44 or to other locations along the length of the lead 32.

In some embodiments, the conductor coil 52 comprises a single filar wire coil formed from an electrically conductive material such as gold or platinum. Alternatively, and in other embodiments, the conductor coil 52 comprises a multi-filar wire coil formed from an electrically conductive material. In the embodiment depicted, the conductive coil 52 has a substantially circular transverse shape perpendicular to the length of the coil 52, which can be seen generally at a cut portion of the assembly 50 indicated by cross-hatching in FIG. 3. In other embodiments, the conductive coil 52 may have an oval, rectangular, square, polygonal, or other transverse shape.

Figure 4:
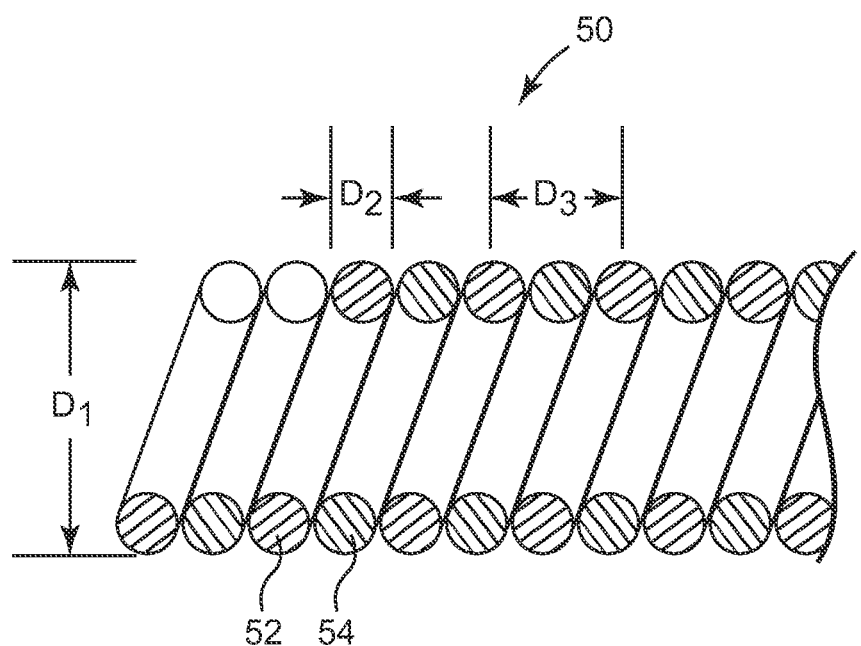
FIG. 4 is a cross-sectional view of the conductor coil assembly along line 4-4 in FIG. 3.

The dimensions of the conductor coil 52 will typically vary depending on the intended use of the lead 32 and the implantation location of the lead 32 within the body. For cardiac applications in which the lead 32 is implanted in or near the heart, and as further shown in FIG. 4, the conductor coil 52 may have an outer diameter $D_1$ in the range of about 0.2 mm to 3.0 mm, although other dimensions are possible. The transverse dimension $D_2$ of the conductor coil 52 may be constant along the length of the coil 52, or can vary along the length of the coil 52. In some embodiments, for example, the conductor coil 52 has a constant transverse dimension $D_2$ in the range of about 0.05 mm to 1.0 mm. In other embodiments, the transverse dimension $D_2$ may vary continuously or at one or more discrete locations along the length of the lead 32. In one embodiment, for example, the transverse dimension $D_2$ may gradually taper from a relatively large dimension (e.g., 1 mm) at or near the proximal end 40 of the lead 32 to a relatively small dimension (e.g., 0.05 mm) at or near the distal end 44 of the lead 32.

The dimensions of the conductor coil 52 may vary depending on the intended use and/or implantation location of the lead 32 within the body. In neurological applications, for example, the conductor coil 52 may have an outer dimension $D_1$ in the range of about 0.2 mm to 3.0 mm, and a transverse dimension $D_2$ in the range of about 0.05 mm to 1.0 mm. The dimensions of the conductor coil 52 will typically vary depending on the anatomy of the patient at the implantation location and the dimensions of the lead 32. Other design factors such as the flexibility of the lead 32, fatigue considerations, manufacturing ease, and the ability to dissipate and/or deflect electromagnetic energy along the length of the lead 32 may also affect the dimensions $D_1,D_2$ of the conductor coil 52.

In the embodiment of FIG. 3, the coil assembly 50 further includes a non-conductive spacer filar 54 helically disposed about the longitudinal axis L of the coil assembly 50 and interstitially disposed between each adjacent turn of the conductive coil 52. In contrast to the conductor coil 52, the spacer filar 54 is formed at least in part of a non-conductive material, and is electrically isolated from the conductor coil 52, the pulse generator 14, and the lead tip electrode or electrodes 46. Examples of electrically non-conductive materials include, but are not limited to, polyurethane, silicon, and polytetrafluoroethylene (PTFE).

Figure 10:
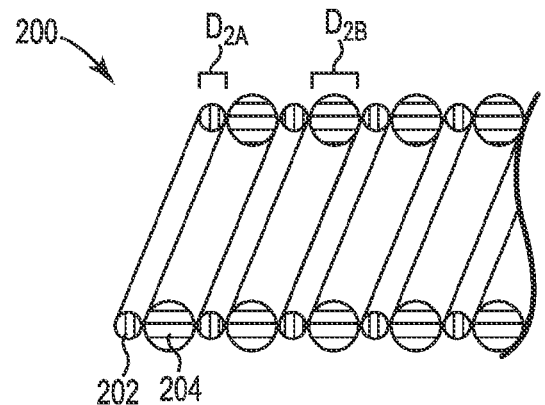
FIG. 10 is a cross-sectional view of a conductor coil assembly.
Figure 11:
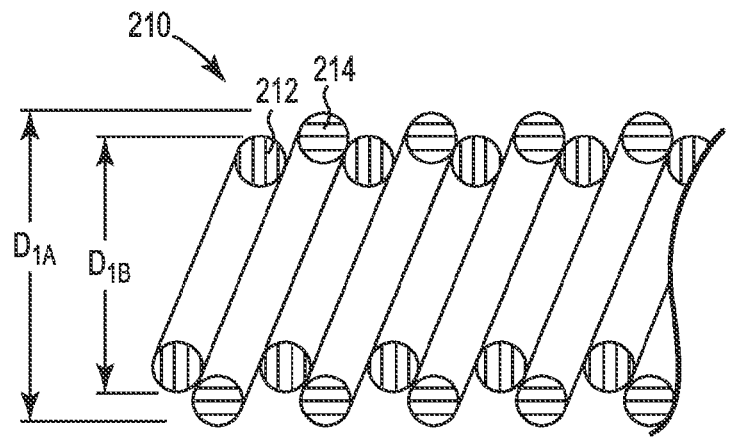
FIG. 11 is a cross-sectional view of a conductor coil assembly.

In some embodiments, the spacer filar 54 has an outer diameter and transverse dimension similar to that of the conductor coil 52. In certain embodiments, for example, the spacer filar 54 has an outer diameter in the range of about 0.2 mm to 3.0 mm, and a transverse dimension in the range of about 0.05 mm to 1.0 mm. In other embodiments, the outer diameter and/or transverse dimension of the spacer filar 54 may differ from the conductor coil 52. For example, FIG. 10 shows a coil assembly 200 comprising a first element 202 and a second element 204, wherein the first element 202 has a smaller transverse dimension D2A than the transverse dimension D2B of the second element 204. The first element 202 can correspond to either of a spacer filar or a conductor coil with the second element 204 can correspond to other of the spacer filar or the conductor coil. In a further example, FIG. 11 shows a coil assembly 210 comprising a first element 212 and a second element 214, wherein the first element 212 has a smaller outer diameter D2B than the outer diameter D1A of the second element 214. The first element 212 can correspond to either of a spacer filar or a conductor coil with the second element 214 can correspond to other of the spacer filar or the conductor coil. The transverse shape of the spacer filar 54 may be similar to the transverse shape of the conductor coil 52, or alternatively, can have a different transverse shape from that of the conductor coil 52.

Figure 12:
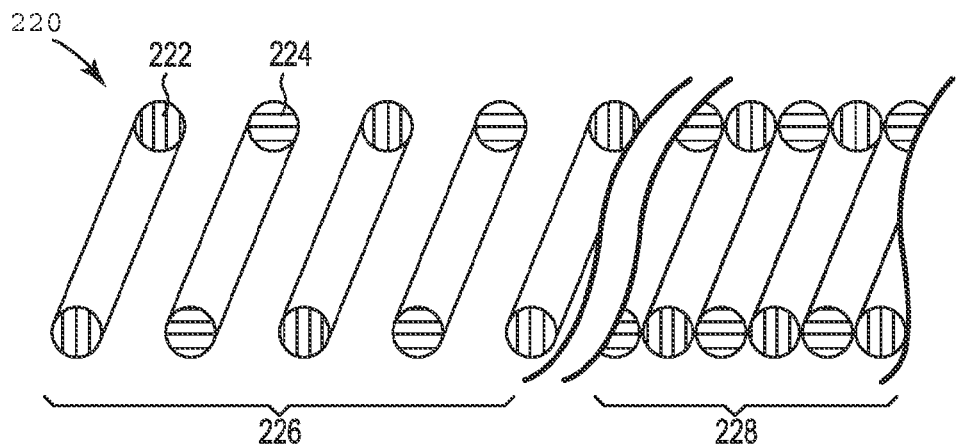
FIG. 12 is a cross-sectional view of a conductor coil assembly.

In some embodiments, the spacer filar 54 is configured to contact each adjacent wire turn of the conductive coil 52, forming a close-wound coil assembly 50 along all or a portion of the length of the lead body 34. As used herein, the term "close-wound" indicates that there are no significant gaps or spaces between any of the turns of the conductive coil 52 or spacer filar 54. In other embodiments, a small gap or spacing may exist between one or more of the spacer filar 54 turns and adjacent conductor coil 52 turns, forming an open-wound coil assembly 50 along all or a portion of the lead body 34. In one embodiment, for example, a first portion of the coil assembly 50 (e.g., a proximal portion) may be close-wound with each spacer filar turn 54 contacting an adjacent conductor coil 52 turn whereas a second portion of the coil assembly 50 (e.g., a distal portion) may be open-wound with each spacer filar turn 54 spaced a distance apart from an adjacent conductor coil 52 to form a small gap or space therebetween. FIG. 12 shows a coil assembly 220 comprising a first element 222 and a second element 224. The first element 222 can correspond to either a spacer filar or a conductor coil with the second element 224 can correspond to other of the spacer filar or the conductor coil. As shown in FIG. 12, a first portion 226 of the coil assembly 220 is open-wound while a second portion 228 of the coil assembly 220 is close-wound.

The coil assembly 50 can be manufactured using medical electrical lead fabrication techniques known in the art. In some embodiments, for example, the coil assembly 50 can be fabricated by drawing a conductive wire and non-conductive wire through a series of dies to impart a desired transverse shape to each wire, and then wrapping both wires together about a mandrel to impart the desired helical shape to the assembly 50. Other lead fabrication techniques are also contemplated.

In use, the presence of the spacer filar 54 between each turn of the conductor coil 52 increases the lateral distance $D_3$ between each of the conductor coil turns 52 while also maintaining the desired flexibility and fatigue characteristics of the coil assembly 50. As a result, the spacing provided by the spacer filar 54 acts to increase the pitch of the conductor coil 52 relative to single-filar conductor coil designs with no interstitial spacer filar, thus reducing the total length of the conductor coil 52 within the lead 32. For example, for a close-wound coil assembly employing a spacer filar 54 having a transverse dimension $D_2$ similar to that of the conductor coil 52, the effective pitch of the conductor coil 52 is approximately twice that of a close-wound conductor coil with no spacer filar. When subjected to electromagnetic or RF energy during an MRI or other such medical procedure, this reduced length of the conductor coil 52 may help to deflect a greater amount electromagnetic energy away from the lead 32, thus reducing the effects of tissue heating within the body.

Figure 5:
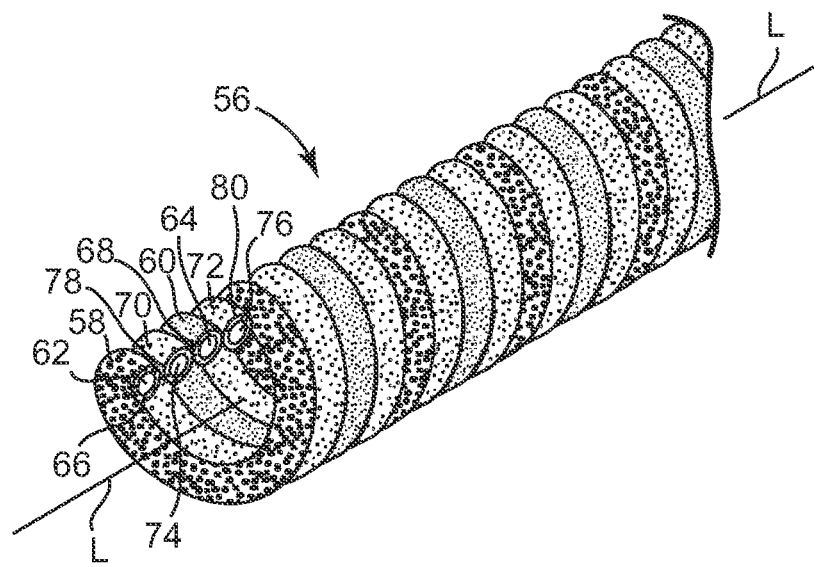
FIG. 5 is a partial cross-sectional view showing another illustrative conductor coil assembly for use with a medical electrical lead.

FIG. 5 is a partial cross-sectional view showing another illustrative coil assembly 56 for use with a medical electrical lead. As shown in FIG. 5, the coil assembly 56 includes a pair of conductor coils 58,60 each helically disposed about the longitudinal axis L of the assembly 56. A first conductor 58 of the coil assembly 56 is coupled proximally to a first electrical feedthrough or connector on the pulse generator 14, and may extend along all or a portion of the length of the lead body 34, terminating distally at a first electrode on the lead 32. A second conductor 60 of the coil assembly 56, in turn, is coupled proximally to a second electrical feedthrough or connector on the pulse generator 14, and may extend along all or a portion of the length of the lead body 34, terminating distally at a second electrode on the lead 32. In use, and in some embodiments, the conductor coils 58,60 can be used in conjunction with a bipolar lead to deliver bipolar electrical energy through the lead body 34 for providing therapy to the patient and/or for sensing parameters such as electrical impedance within the patient's body. In some embodiments, for example, the conductor coils 58,60 may function, respectively, as anode and cathode electrodes to deliver bipolar electrical energy to body tissue adjacent to the distal lead tip 44 or to other locations along the length of the lead 32.

The configuration of the conductor coils 58,60, including the shape and/or dimensions of the conductors 58,60, may be similar to that of the conductor coil 52 of FIG. 3. Alternatively, and in other embodiments, the shape and/or dimensions of the conductor coils 58,60 may vary from the conductor coil 52. In the embodiment of FIG. 5, each of the conductor coils 58,60 comprises an insulated wire having an inner core 62,64 of electrically conductive material such as gold or platinum. In some embodiments, each of the conductor coils 58,60 include a layer or coating 66,68 of electrically non-conductive material disposed about the inner core 62,64. For example, the conductor coils 58,60 can include a layer or coating 66,68 of polyurethane, silicon, or polytetrafluoroethylene (PTFE) disposed about an inner core 62,64 of gold or platinum. Other configurations, however, are possible.

The coil assembly 56 further includes a number of non-conductive spacer filars 70,72 interstitially disposed between laterally adjacent turns of the conductor coils 58,60. Each of the spacer filars 70,72 are formed at least in part of an electrically non-conductive material, and are electrically isolated from the conductor coils 58,60, the pulse generator 14, and the lead tip electrode or electrodes 46. The configuration of the spacer filars 70,72, including the shape and/or dimensions of the spacer filars 70,72 may be similar to that of the spacer filar 54 of FIG. 3. Alternatively, and in other embodiments, the shape and/or dimensions of the spacer filars 70,72 may differ from the spacer filar 54 of FIG. 3.

In the embodiment of FIG. 5, each of the spacer filars 70,72 comprises a respective inner core 74,76 made from an electrically conductive material, and an outer layer or coating 78,80 made from an electrically non-conductive material. For example, in some embodiments each of the spacer filars 70,72 can be fabricated from a gold or platinum wire jacketed or coated with polyurethane, silicon, or polytetrafluoroethylene (PTFE) shielding.

As with the embodiment of FIG. 3, the presence of the spacer filars 70,72 between the turns of the conductor coils 58,60 increases the pitch of the coils 58,60, which in turn, reduces the length of the conductor coils 58,60. This reduced length of the conductor coils 58,60 may help to deflect a greater amount of electromagnetic energy away from the lead 32, thus reducing the effects of tissue heating within the body. The presence of the inner core 74,76 of conductive material within the spacer filars 70,72 may further help to collect and dissipate electromagnetic energy received by the lead 32, further reducing the effects of tissue heating within the body.

Figure 6:
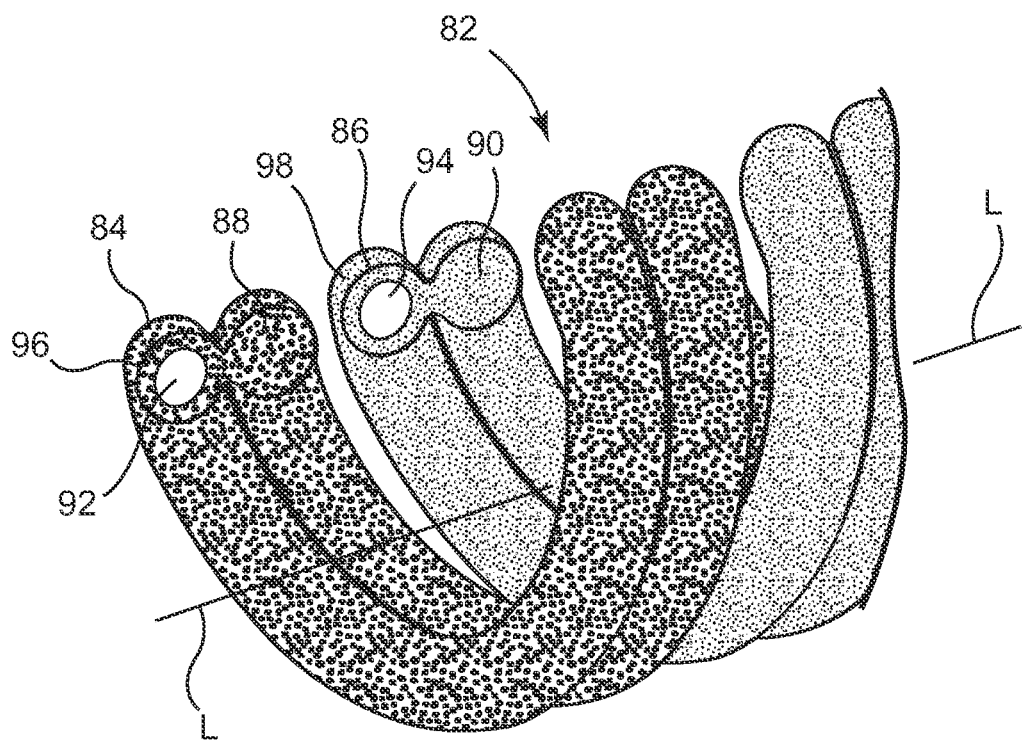
FIG. 6 is a partial cross-sectional view showing another illustrative conductor coil assembly for use with a medical electrical lead.

FIG. 6 is a partial cross-sectional view showing another illustrative coil assembly 82 for use with a medical electrical lead. As shown in FIG. 6, the coil assembly 82 includes a pair of conductor coils 84,86 each helically disposed about the longitudinal axis L of the assembly 82. A first conductor 84 of the assembly 82 is coupled proximally to a first electrical feedthrough or connector on the pulse generator 14, and may extend along all or a portion of the length of the lead body 34, terminating distally at a first electrode on the lead 32. A second conductor 86 of the assembly, in turn, is coupled proximally to a second electrical feedthrough or connector on the pulse generator 14, and may extend along all or a portion of the length of the lead body 34, terminating distally at a second electrode on the lead 32. In some embodiments, the conductor coils 84,86 can be configured for use in a bipolar lead to deliver bipolar electrical energy through the lead body 34 that can be used to provide therapy to the patient and/or for sensing parameters such as electrical impedance within the patient's body.

In the embodiment of FIG. 6, each of the conductor coils 84,86 includes an associated spacer filar 88,90 coupled to or formed integrally with the conductor coils 84,86. In some embodiments, for example, each of the conductor coils 84,86 is formed from an inner core 92,94 of electrically conductive material (e.g., gold or platinum) and an outer layer or coating 96,98 of an electrically non-conductive material. In one embodiment, fabrication of each of the conductor coils 84,86 is accomplished via a co-extrusion process in which the outer, non-conductive layer or coating 96,98 (including the material forming the spacer filar 88,90) is co-extruded with the inner core 92,94 material, forming a non-symmetric extrusion (e.g., a dumb-bell shape) over the conductor coils 84,86. Other techniques such as over-molding the outer layer or coating 96,98 over the inner wire core 92,94 material can also be used to fabricate each of the conductor coils 84,86.

Figure 7:
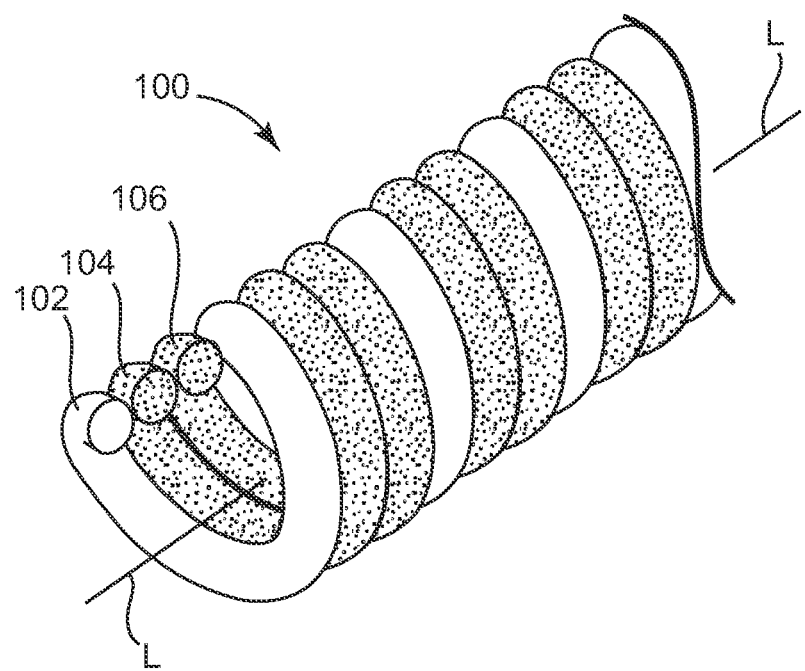
FIG. 7 is a partial cross-sectional view showing another illustrative conductor coil assembly for use with a medical electrical lead.

FIG. 7 is a partial cross-sectional view showing another illustrative coil assembly 100 for use with a medical electrical lead. The coil assembly 100 is similar to the coil assembly 50 of FIG. 3, including a single filar conductor coil 102 helically disposed about the longitudinal axis L of the assembly 100. In the embodiment of FIG. 7, however, the coil assembly 100 includes a pair of non-conductive spacer filars 104,106 interstitially disposed between each laterally adjacent turn of the conductive coil 102. The spacer filars 104,106 can be formed from a solid wire coil, or alternatively can be formed from an inner core of electrically conductive material and one or more outer layers or coatings of an electrically non-conductive material.

In use, and as with other embodiments herein, the presence of the spacer filars 104,106 between each coil turn of the conductor coil 102 functions to increase the pitch of the conductor coil 102 while also maintaining the flexibility and fatigue characteristics of the coil assembly 100. This increase in pitch reduces the total length of the conductor coil 102 along the length of the lead 32, which may help to deflect a greater amount of electromagnetic energy away from the lead 32.

Figure 8:
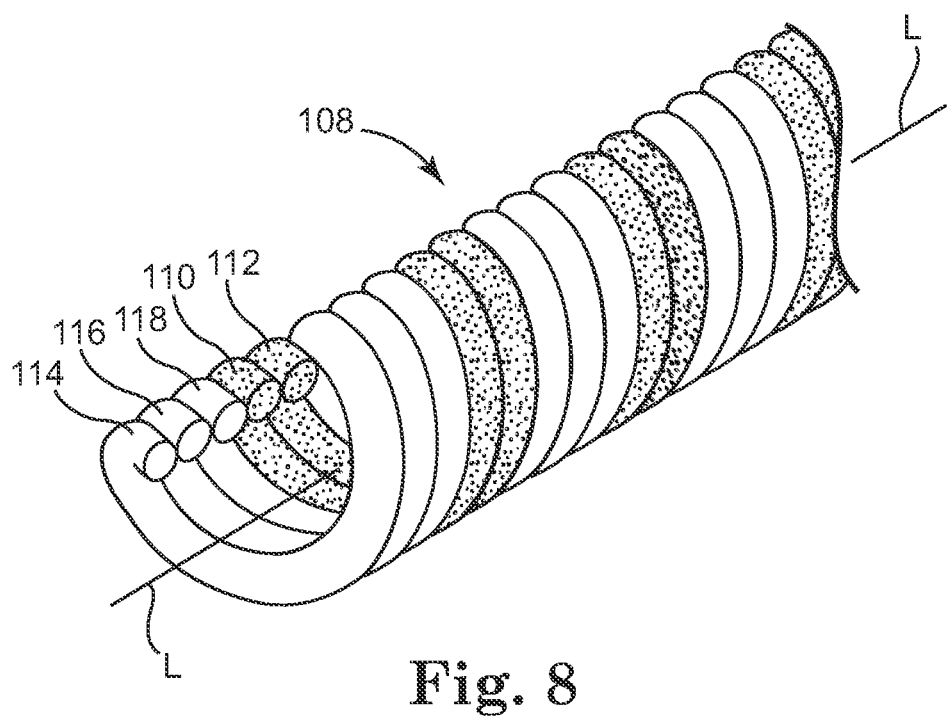
FIG. 8 is a partial cross-sectional view showing another illustrative conductor coil assembly for use with a medical electrical lead.

The number of conductor coils and/or spacer filars can be varied to produce other coil assemblies. In one embodiment depicted in FIG. 8, for example, the coil assembly 108 includes two conductor coils 110,112 and three spacer filars 114,116,118. The coil assembly 108 can include a greater or lesser number of spacer filars and/or conductor coils. For example, in some embodiments the coil assembly includes a single filar conductor coil having two or more non-conductive spacer filars interstitially disposed between each coil turn of the conductor coil. Alternatively, and in other embodiments, the coil assembly includes multiple conductor coils (e.g., two, three, four, etc.) with one or more spacer filars interstitially disposed between each conductor coil turn.

Figure 9:
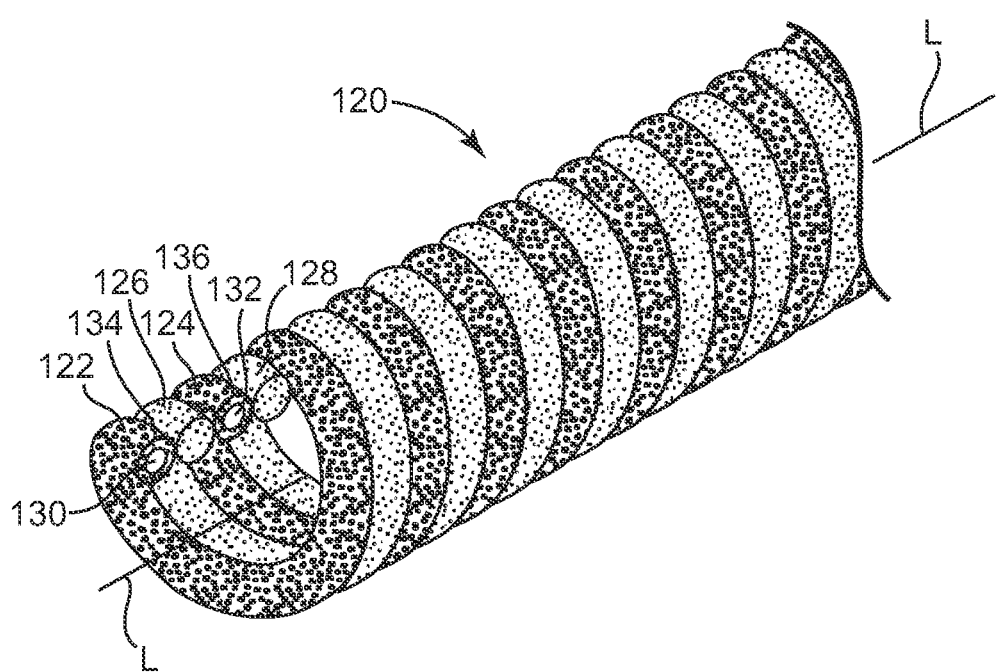
FIG. 9 is a partial cross-sectional view showing another illustrative conductor coil assembly for use with a medical electrical lead.

FIG. 9 is a partial cross-sectional view showing another illustrative coil assembly 120 for use with a medical electrical lead. As shown in FIG. 9, the coil assembly 120 includes a pair of conductor coils 122,124 and a pair of spacer filars 126,128. The conductor coils 122,124 may each be coupled proximally to electrical feedthroughs or connectors on the pulse generator 14, and may extend along all or a portion of the length of the lead body 34, terminating distally at a respective set of electrodes on the lead 32. In some embodiments, for example, the conductor coils 122,124 can be configured for use in bipolar leads to deliver bipolar electrical energy through the lead body 34 for providing therapy to the patient and/or for sensing parameters such as electrical impedance within the patient's body.

The configuration of the conductor coils 122,124, including the shape and/or dimensions of the coils 122,124 may be similar to that of the conductor coil 52 of FIG. 3. Alternatively, and in other embodiments, the shape and/or dimensions of the conductor coils 122,124 may vary from the conductor coil 52. In the embodiment of FIG. 9, each of the conductor coils 122,124 comprises an insulated wire having an inner core 130,132 of electrically conductive material, and an outer layer or coating of electrically non-conductive material 134,136. In other embodiments, the conductor coils 122, 124 may each comprise a solid, conductive material with no insulation.

In the embodiment of FIG. 9, the spacer filars 126,128 are each interstitially disposed between laterally adjacent turns of the conductor coils 122,124. The spacer filars 126,128 can be configured to contact each adjacent turn of the conductor coil 122,124, as shown, or can be spaced apart from each adjacent turn of the conductor coil 122,124 via a small gap or spacing. In some embodiments, the spacer filars 126,128 can be formed from a solid coil of electrically non-conductive material. In other embodiments, the spacer filars 126,128 can be formed from an inner core of electrically conductive material and one or more outer layers or coatings of an electrically non-conductive material.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A medical electrical lead, comprising:
   a lead body having a proximal section and a distal section;
   an electrode coupled to the distal section of the lead body;
   at least one helically coiled electrical conductor disposed within an interior lumen of the lead body and electrically coupled to the electrode, the at least one helically coiled electrical conductor including a plurality of turns disposed about a longitudinal axis of the lead body and extending from the proximal section to the distal section of the lead body;
   at least one helically coiled spacer element electrically isolated from the electrode, the at least one helically coiled spacer element including a plurality of turns interstitially disposed between adjacent turns of the at least one helically coiled electrical conductor to form a coil assembly comprising the at least one helically coiled electrical conductor and the at least one helically coiled spacer element; and
   wherein the at least one helically coiled electrical conductor and the at least one helically coiled spacer element are wound together to have a first portion of the coil assembly that is close-wound and a second portion of the coil assembly that is open-wound.

2. The medical electrical lead of claim 1, wherein the at least one helically coiled electrical conductor comprise a plurality of conductor wires each including a plurality of wire turns.

3. The medical electrical lead of claim 1, wherein the at least one helically coiled electrical conductor comprises a single conductor wire including a plurality of wire turns.

4. The medical device of claim 1, wherein the at least one helically coiled electrical conductor extends from the electrode to a proximal lead connector.

5. The medical electrical lead of claim 1, wherein the at least one helically coiled spacer element includes a single polymeric filar.

6. The medical electrical lead of claim 1, wherein the at least one helically coiled spacer element includes a plurality of polymeric filars.

7. The medical electrical lead of claim 1, wherein the at least one helically coiled spacer element includes at least one insulated metal filar.

8. The medical electrical lead of claim 1, wherein the at least one helically coiled spacer element contacts each adjacent turn of the at least one helically coiled electrical conductor along the first portion of the coil assembly such that there are no significant gaps or spaces between any adjacent turns.

9. The medical electrical lead of claim 8, wherein each turn of the at least one helically coiled spacer element is spaced a distance apart from each adjacent turn of the at least one helically coiled electrical conductor along the second portion of the coil assembly such that space exists between adjacent turns of the at least one helically coiled spacer element and the at least one helically coiled electrical conductor.

10. The medical electrical lead of claim 1, wherein each electrical conductor and spacer element has a transverse dimension, and wherein the transverse dimension of the electrical conductor is different than the transverse dimension of the spacer element.

11. The medical electrical lead of claim 1, where each electrical conductor and spacer element has an outer diameter, and wherein the outer diameter of the electrical conductor is different than the outer diameter of the spacer element.

12. The medical electrical lead of claim 1, wherein the first portion of the coil assembly is proximal of the second portion of the coil assembly.

13. The medical electrical lead of claim 1, wherein each electrical conductor has an outer diameter from about 0.2 mm to about 3.0 mm and a transverse dimension from about 0.05 mm to about 1.0 mm.

14. The medical electrical lead of claim 1, wherein each spacer element has an outer diameter from about 0.2 mm to about 3.0 mm and a transverse dimension from about 0.05 mm to about 1.0 mm.

15. A medical electrical lead, comprising:
   a lead body having a proximal section and a distal section;
   an electrode coupled to the distal section of the lead body;
   a helically coiled electrical conductor disposed within an interior lumen of the lead body and electrically coupled to the electrode, the electrical conductor including a plurality of turns disposed about a longitudinal axis of the lead body and extending from the proximal section to the distal section of the lead body;
   a helically coiled spacer element electrically isolated from the electrode, the spacer element including a proximal end, a distal end, and a plurality of turns interstitially disposed between adjacent turns of the electrical conductor, the proximal end of the spacer element located within the distal section of the lead body and extending to a distal lead tip of the lead to form a coil assembly comprising the electrical conductor and the spacer element; and
   wherein the electrical conductor and the spacer element are wound together to have a first portion of the coil assembly that is close-wound and a second portion of the coil assembly that is open-wound.

16. A medical electrical lead, comprising:
   a lead body having a proximal section and a distal section;
   an electrode coupled to the distal section of the lead body;
   a helically coiled electrical conductor disposed within an interior lumen of the lead body and electrically coupled to the electrode, the conductor wire having a transverse shape and including a plurality of wire turns disposed about a longitudinal axis of the lead body;
   a helically coiled spacer element electrically isolated from the electrode and including a plurality of turns interstitially disposed between adjacent turns of the electrical conductor to form a coil assembly comprising the electrical conductor and the spacer element; and
   wherein the electrical conductor and the spacer element are wound together to have a first portion of the coil assembly and a second portion of the coil assembly, the first portion having different spacing between adjacent turns of the electrical conductor and the spacer element relative to the second portion.

17. The medical electrical lead of claim 16, wherein the first portion has closed-spacing and the second portion has open spacing.

18. The medical electrical lead of claim 16, where the electrical conductor and spacer element each have an outer diameter, and wherein the outer diameter of the electrical conductor is different than the outer diameter of the spacer element.

19. The medical electrical lead of claim 16, wherein the electrical conductor has an outer diameter from about 0.2 mm to about 3.0 mm and a transverse dimension from about 0.05 mm to 1.0 mm.

20. The medical electrical lead of claim 16, wherein the spacer element has an outer diameter from about 0.2 mm to about 3.0 mm and a transverse dimension from about 0.05 mm to 1.0 mm.

* * * * *